(12) United States Patent
Edhouse et al.

(10) Patent No.: US 8,961,463 B2
(45) Date of Patent: Feb. 24, 2015

(54) DEVICE FOR THE AUTOMATIC INJECTION OF TWO DOSES OF A MEDICAMENT

(75) Inventors: Mark Jeffrey Edhouse, Cambridge (GB); Patrick J. Ryan, West Hollywood, CA (US); Max William Middleton, London (GB); Christopher Edward Butcher, Cambridge (GB)

(73) Assignee: Menarini International Operations Luxembourg S.A., Luxembourg (LU)

( * ) Notice: Subject to any disclaimer, the term of this patent is extended or adjusted under 35 U.S.C. 154(b) by 403 days.

(21) Appl. No.: 13/579,747

(22) PCT Filed: Mar. 9, 2011

(86) PCT No.: PCT/IB2011/050985
§ 371 (c)(1),
(2), (4) Date: Nov. 12, 2012

(87) PCT Pub. No.: WO2011/111006
PCT Pub. Date: Sep. 15, 2011

(65) Prior Publication Data
US 2013/0046238 A1    Feb. 21, 2013

(30) Foreign Application Priority Data
Mar. 10, 2010   (IT) ................ FI2010A0033

(51) Int. Cl.
*A61M 5/20*     (2006.01)
*A61M 5/315*    (2006.01)
*A61M 5/32*     (2006.01)

(52) U.S. Cl.
CPC ............. *A61M 5/31595* (2013.01); *A61M 5/20* (2013.01); *A61M 5/31578* (2013.01);
(Continued)

(58) Field of Classification Search
CPC ... A61M 5/20; A61M 5/315; A61M 5/31525; A61M 5/31526; A61M 2005/2013; A61M 2005/2026
USPC .......................... 604/134–137, 208–210, 218
See application file for complete search history.

(56) References Cited

U.S. PATENT DOCUMENTS

| 4,031,893 A | 6/1977 | Kaplan et al. |
| 5,665,071 A | 9/1997 | Wyrick |

(Continued)

FOREIGN PATENT DOCUMENTS

| EP | 651662 | 10/1995 |
| EP | 0700307 | 3/1996 |

(Continued)

OTHER PUBLICATIONS

PCT International Search Report mailed on Sep. 5, 2011 for PCT/IB2011/050985 filed on Mar. 9, 2011 in the name of Menarini International Operations Luxembourg S.A.
(Continued)

*Primary Examiner* — Laura Bouchelle
(74) *Attorney, Agent, or Firm* — Steinfl & Bruno, LLP

(57) ABSTRACT

A two-dose autoinjector for a medicament wherein the locking and releasing of the drive spring of the autoinjector is controlled through stepped guides with ramps for two successive slidings of slides operated by the spring and connected with the syringe and plunger. The guides and the slides are pivotable relative to one another and the sliding direction, while the syringe can only slide axially. To enable or disable the sliding of the slides within the guides an angularly angularly mobile arming member is provided formed with a guide track substantially equal to that of the stationary member where the guides are formed.

18 Claims, 13 Drawing Sheets

(52) U.S. Cl.
CPC .......... *A61M 5/326* (2013.01); *A61M 2005/206* (2013.01); *A61M 2005/2013* (2013.01)
USPC ........................... 604/137; 604/135; 604/208

(56) References Cited

U.S. PATENT DOCUMENTS

| | | | |
|---|---|---|---|
| 6,575,939 | B1 | 6/2003 | Brunel |
| 7,396,347 | B2 * | 7/2008 | Hjertman et al. ............. 604/207 |
| 7,597,685 | B2 * | 10/2009 | Olson ........................... 604/208 |
| 7,717,877 | B2 * | 5/2010 | Lavi et al. .................... 604/137 |
| 7,976,514 | B2 * | 7/2011 | Abry et al. ................... 604/246 |
| 8,376,993 | B2 * | 2/2013 | Cox et al. ..................... 604/110 |

FOREIGN PATENT DOCUMENTS

| | | |
|---|---|---|
| WO | 94/26331 | 11/1994 |
| WO | 94/27660 | 12/1994 |

OTHER PUBLICATIONS

PCT Written Opinion mailed on Sep. 5, 2011 for PCT/IB2011/050985 filed on Mar. 9, 2011 in the name of Menarini International Operations Luxembourg S.A.

\* cited by examiner

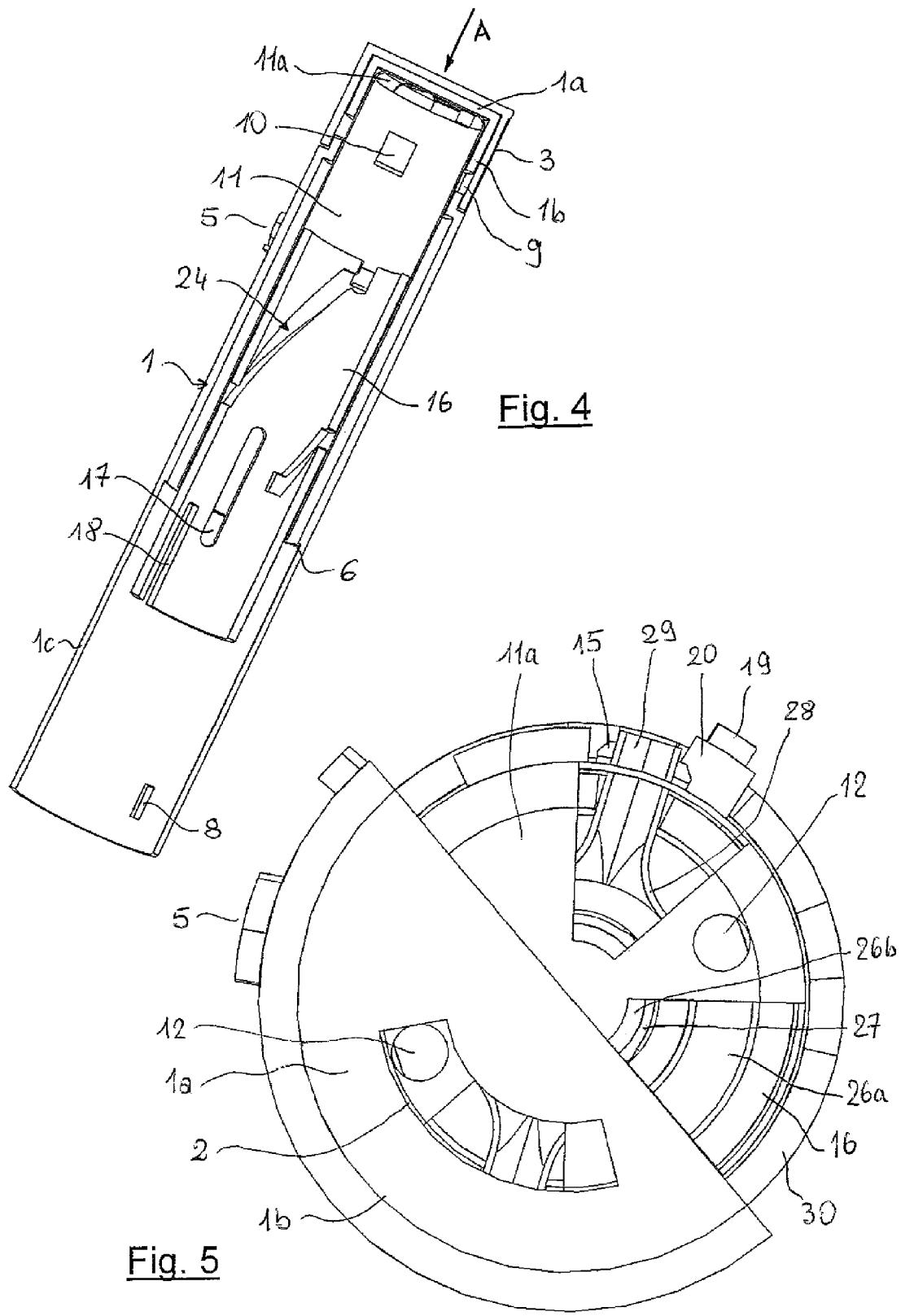

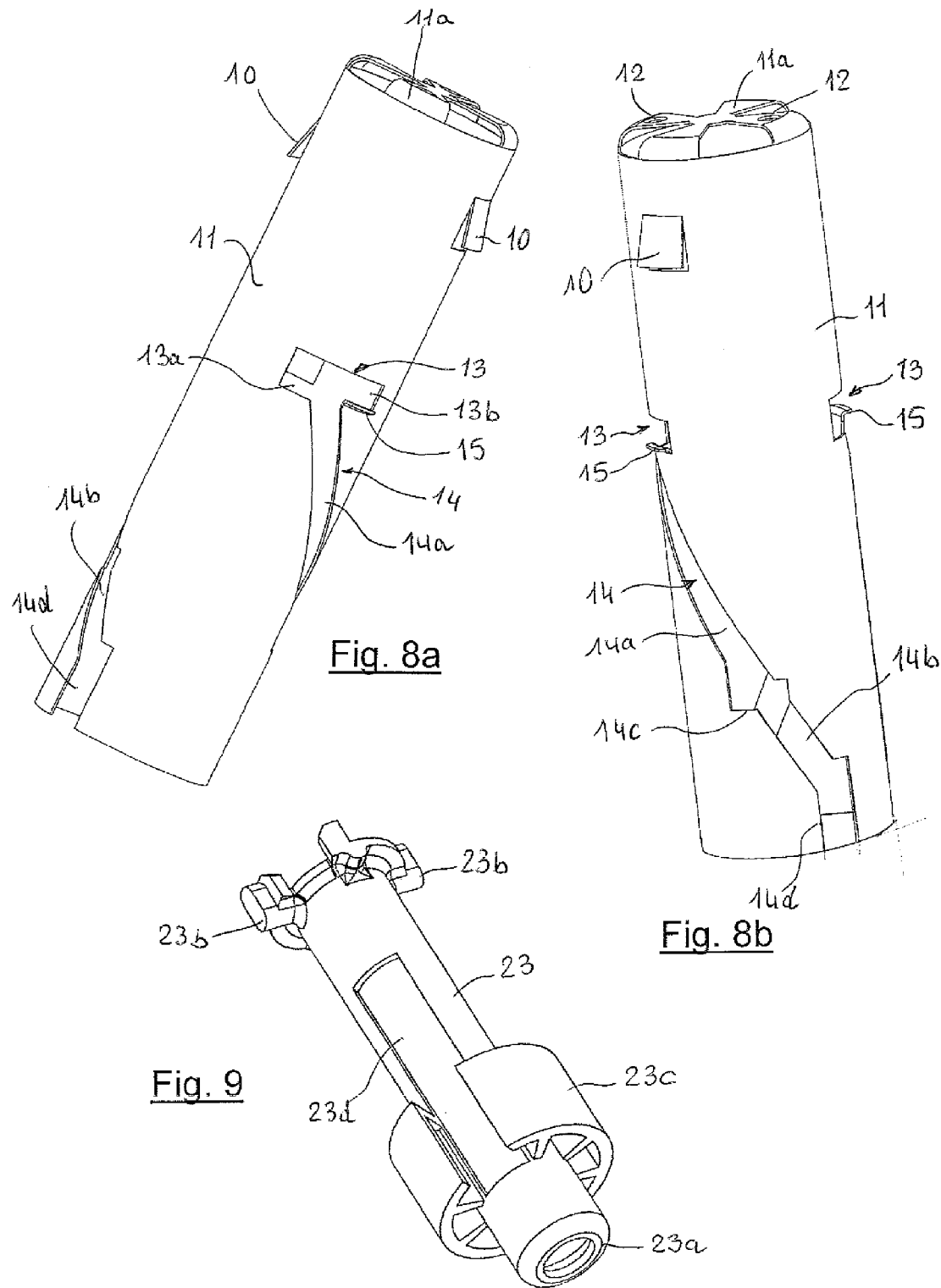

DEVICE FOR THE AUTOMATIC INJECTION OF TWO DOSES OF A MEDICAMENT

CROSS REFERENCE TO RELATED APPLICATIONS

The present application is the US national stage of International Application PCT/IB2011/050985 filed on Mar. 9, 2011 which, in turn, claims priority to Italian Patent Application FI2010A000033 filed on Mar. 10, 2010.

FIELD OF THE INVENTION the present application is the US national stage of International Application PCT/IB2011/050985 files on Mar. 9, 2011 which, in turn, claims priority to Italian Patent Application FI2010A000033 filed on Mar. 10,2010

The present invention relates generally to devices for the injection of medicaments and more precisely relates to a device for the automatic injection of medicaments especially a medicament for allergic emergencies, such as epinephrine or adrenaline, according to a requested time sequence. In particular, the invention refers to a device for the automatic injection of two doses of a medicament at two successive times.

BACKGROUND OF THE INVENTION

Many devices of the above mentioned type allowing a patient to self-administer one or more (generally two) doses of a medicament are known. U.S. Pat. No. 6,575,939 discloses an autoinjector device comprising a syringe housed in a casing formed by an inner part and an outer part capable of sliding in relation to each other. By pressing the end of the inner part (the needle outlet end) against the patient's skin at the injection site, the outer part slides forward along the inner part, thus unlocking a push-button. By depressing the button, the syringe and the relevant plunger are triggered to first thrust in the needle and then deliver the medicament. The needle retraction in the casing is obtained by stopping pressing the outer part end against the skin. This autoinjector allows a single dose of medicament to be administered.

An autoinjector device for automatic administering a single dose of a medicament is also known from U.S. Pat. No. 4,031,893. The autoinjector is equipped with an unlocking device with a deformable member for the driving device. The syringe plunger is axially connected to a rod comprising four flexible axial arms having a toothed end engaged on the edge of an opening formed on a cap placed at the end of the syringe housing. Cap sliding causes the arm ends to deform and their teeth to release from the opening edge. In this way the driving device is triggered. The autoinjector according to this document also comprises a safety device to prevent accidental deformation of the arm ends and triggering of the driving device, consisting of an insert centrally extending from the cap and capable of coming between the rod arms to prevent them from bending.

EP700307 discloses a two-dose autoinjector allowing the automatic delivering of a first dose of a medicament and the manual administration of a second dose. The autoinjector device according to this patent foresees the use of a syringe housed slidably in a tubular housing in two parts that can be separated to allow positioning of the syringe containing two doses of the medicament to be delivered and removal after use. The sliding of the syringe in the housing to penetrate the needle and inject the medicament is operated by an actuator movable between an armed position and an extended position. A releasable locking device is provided to limit the syringe plunger sliding to an extent corresponding to the volume of the first dose. The syringe is mounted in the tubular housing in a movable way to enable the locking device to be removed after the first dose is delivered and the plunger drive means to be armed again, if the second dose is to be automatically administered, or the syringe to be removed, if the second dose is to be manually administered. Furthermore the drive means is provided with a safety lock formed by a member engaging with a deformable pin of the drive means to keep it in a deformed condition, thereby preventing it to trigger. An autoinjector of this type is commercially available under the trade mark Twinject® and allows the first dose to be administered automatically, but the second dose must be manually administered.

The autoinjector according to EP651662 is designed to carry out a sequence of injections from a single syringe that is capable of performing a limited sliding movement in a tubular housing. The syringe has a plunger to deliver doses of a medicine through the needle and spring drive means engage with a piston rod and, once they are armed, retain the rod in a first position, while, when they are triggered, cause the rod to move forward and this causes first the syringe sliding and needle projection and then a controlled sliding of the plunger to deliver a medicine dose. Manual arming means are provided and means to trigger again the spring drive means.

The plunger rod has a toothed profile on which a catch of the drive means engages and the syringe is housed in a bushing capable of moving in a limited way in the tubular housing and provided with a further catch that is also engaged with the toothed profile of the rod. When the device is armed by the manual arming means, both the drive means and the bushing in which the syringe is placed are displaced toward the rear end of the tubular housing, the two catches engaging with the toothed profile of the rod. An axial groove connection between the bushing and the drive means allows a further sliding between the catch integral to the drive means and the toothed profile of an extent equal to the pitch of the profile. When the device is triggered, first the drive means cause the syringe bushing to slide up to a front stop and then the rod start sliding relative to the bushing catch for an extent corresponding to the profile pitch, whereby the displacement of a volume of medicine is enabled together with its deliver through the needle.

There is a strong need for an injector device for the automatic injection of a medicament in two successive doses which is user-friendly and is easier to manufacture as compared to the conventional devices. The object of the present invention is therefore to meet these requirements by providing a medicament autoinjector device capable of enabling the patient to self-administering two successive doses of a medicament in the easiest possible way, thus sparing the patient of performing potentially dangerous, complex dismounting/re-arming operations.

SUMMARY OF THE INVENTION

The basic idea of the invention is to control the locking and releasing of the drive spring of the autoinjector by providing stepped guide means with ramps for two successive slidings therealong of slide means operated by the spring and connected with the syringe and relevant plunger. The guide means and the slide means are pivotable relative to one another and the sliding direction, while the syringe can only slide axially, and the triggering control for each sliding is obtained by pressing a trigger, axially slidable relative to a stationary member, against the patient's skin to push the slide means first into one ramp and then into the other ramp of the guide means.

To enable or disable the sliding of the slide means within the guide means a angularly mobile arming member is provided formed with a guide track substantially equal to that of the stationary member where the guide means are formed. Following two subsequent angular arming displacements of the mobile member relative to the stationary member the ramps and the guide track are radially aligned to enable the slide means to slide under the action of the spring and therefore deliver the first dose and then the second dose.

According to one aspect of the invention, the injector device comprises a syringe assembly containing the medicament to deliver and arranged coaxially and slidably within an outer housing extending along a longitudinal axis and means for arming the device from a rest position to a first dose injecting armed position and a second dose injecting armed position, the device arming means being placed at one end of the outer housing. First elastic means that are in a compressed state when the device is in the rest position are provided between the syringe assembly and the device arming means. Device drive means are further provided for controlling the sliding of the syringe assembly from the armed positions to inject the syringe needle in an injection site and deriver the first dose and, if necessary, to deliver the second dose at a prefixed successive time.

The syringe assembly comprises a slide means engaged in stepped guide means inclined, but not incident, with respect to the direction of the longitudinal axis X and axially integral to the outer housing. The slide means and the guide means are pivotable relative to each other about the longitudinal axis and the drive means are axially slidable following separate and subsequent pressures against the injection site, thus causing a first relative displacement of the slide means from the first dose injecting armed position to a guide means alignment position, whereby the slide means is free to run therealong up to a first stop position, and a second relative displacement of the slide means from the second dose injecting armed position to a guide means alignment position, whereby the slide means is free to run therealong up to a second stop position.

In a preferred embodiment, the slide means is axially and pivotally mounted on the syringe assembly, the guide means are rotationally integral with the outer housing and the stepped guide means comprise an inner housing on which an inclined guide track with an intermediate land is formed, said land separating a first and a second inclined guide tract, and two end lands, on which the slide means rests in the first dose injecting armed position and, respectively, after delivering the second dose.

According to another aspect of the invention, the drive means comprise axial legs configured to act on the slide means to displace it from the first dose injecting armed position and, subsequently, from the second dose injecting armed position following corresponding axial movements of the drive means. In particular the drive means comprise a triggering slide movably arranged between the outer housing and the inner housing and projecting from the other end of the outer housing, and second elastic means are provided between the syringe assembly and the triggering slide to keep the latter projecting out of the outer housing.

Preferably, the triggering slide, comprises two diametrically opposed pairs of axial legs for causing the first displacement and, respectively, the second displacement of the slide means. In an embodiment of the invention the arms have a sloped profile and a length substantially equal to that of the first inclined tract and, respectively, the second inclined tract of the guide means.

Further features of the autoinjector device according to the invention are set forth in the attached claims.

BRIEF DESCRIPTION OF THE DRAWINGS

Further features and advantages of the autoinjector device according to the invention will be apparent from the following description of an exemplifying, non-limiting embodiment thereof with reference to the attached drawings, in which:

FIG. 4 is a longitudinal sectional view of the device for arming the autoinjector according to the invention;

FIG. 5 is an axial view in the direction of arrow A of FIG. 4 (cap removed) of the autoinjector device according to the invention;

FIGS. 8a and 8b show, in two perspective views axially rotated by 90°, a tubular member of the autoinjector device according to the invention;

FIG. 9 is a perspective view of the syringe support of the autoinjector device according to the invention;

DETAILED DESCRIPTION OF THE INVENTION

Figure 1:
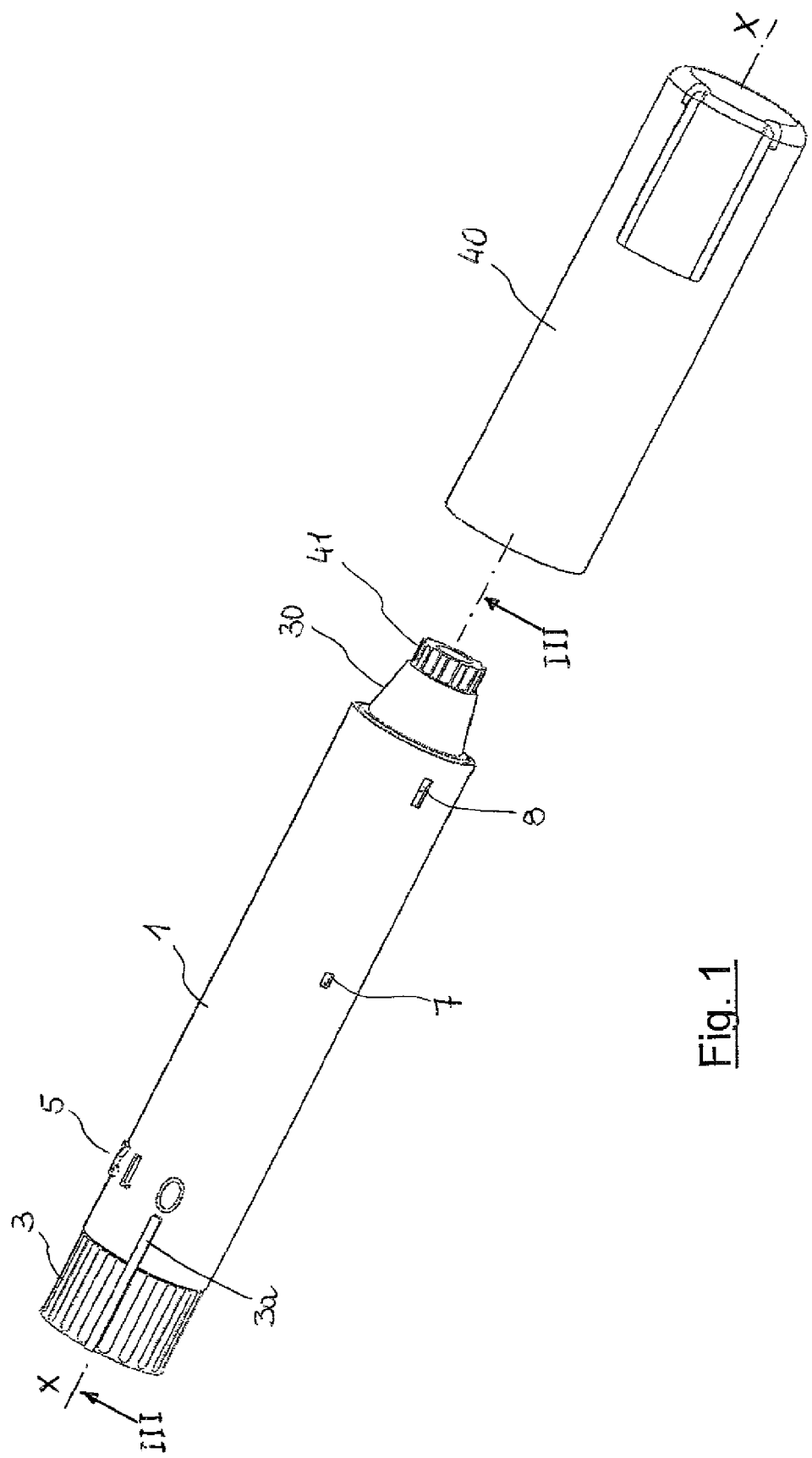
FIG. 1 is an overall side view of the autoinjector device according to the invention, shown separated from its protective sheath.
Figure 2:
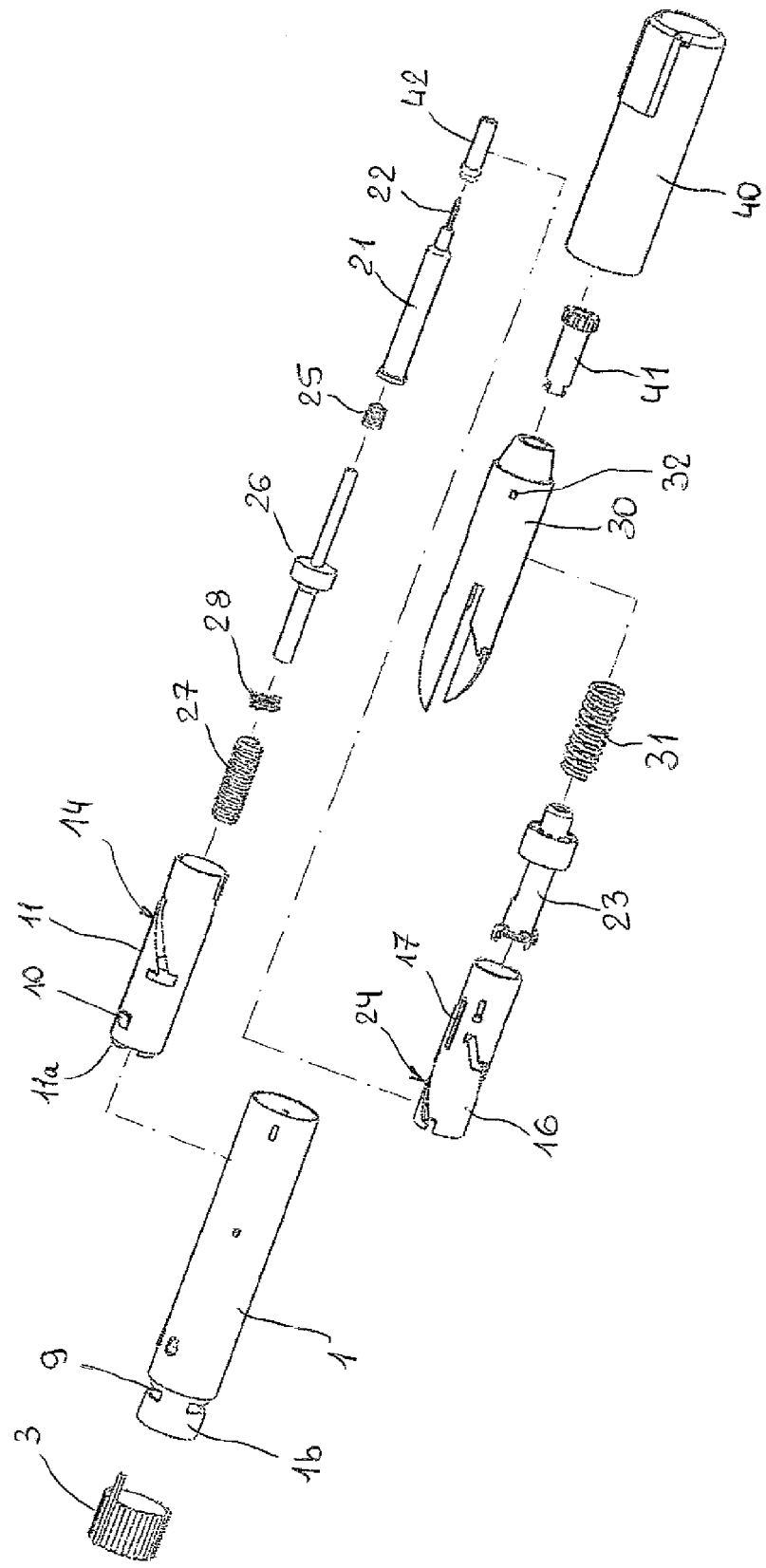
FIG. 2 is a simplified, exploded view of the autoinjector device according to the invention.

With reference to FIGS. 1 and 2, the autoinjector device according to the invention comprises an outer housing 1, having a tubular shape and equipped with a cap-shaped knob 3 at one end, while a tapered end of a trigger slide 30, internal to the outer housing 1, projects from the other end. The tapered end is closed by a needle cap 41 and an inner needle shield 42 sitting directly over the needle is housed in the needle cap 41. Needle cap 41 and needle shield 42 are easily removable when the device is to be used in order to expose the needle ready for the first dose injection. The autoinjector is further provided with a protective sheath 40 sitting over the outer housing 1 when the device is in the storage state.

Figure 3:
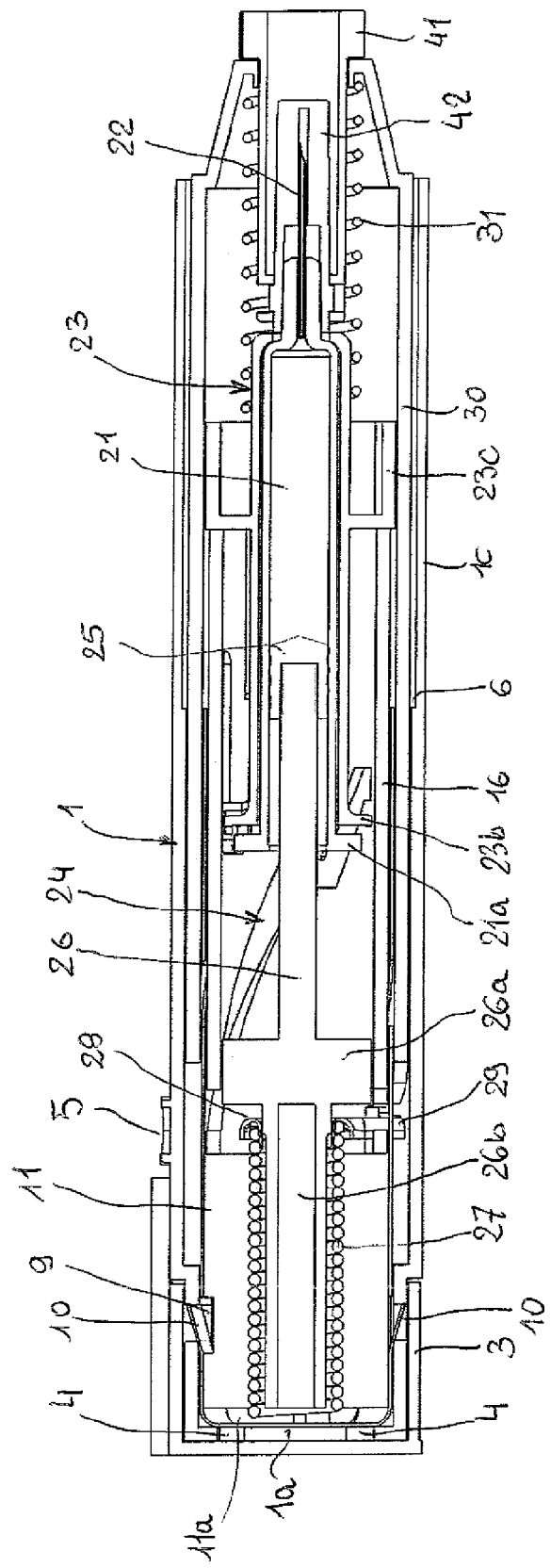
FIG. 3 is a longitudinal sectional view of the autoinjector device according to the invention taken along lines III-Ill of FIG. 1.

With reference also to FIGS. 3 and 4, the outer housing 1 extends over a longitudinal axis X between an open (or distal) end and a closed (or proximal) end, having a closure wall 1a, on which two diametrically opposed, arc grooves 2 (only one shown in FIG. 5) are formed each having an angular extension of, for example, about 90°. The outer housing 1 further has an end portion 1b at its closed end with a lower diameter and defining a surface acting as a seat for the cap-shaped knob 3. Two pins 4 engaging with grooves 2 extend from the bottom side of the knob 3. The knob 3 is mounted coaxially to the outer housing 1 and is pivotable on the end portion 1b of the outer housing 1 and the extent of its clockwise or anticlockwise, angular displacement depends on the angular extension of the grooves 2.

A rod 3a extends from knob 3 parallel to longitudinal axis X along the outer housing 1. Rod 3a serves as pointer to indicate the actual operating condition of the autoinjector device (stored state, first triggerable state, i.e. ready for the first injection, second triggerable state, i.e. ready for the second injection) in combination to as many corresponding reference marks 5 (for instance consisting of reference numerals 0, 1, 2) arranged in a circumferential line on the surface of outer housing 1.

A portion 1c of the outer housing 1, extending from its open end, is formed with a greater inner diameter than the remaining part of the outer housing 1, whereby a circular step 6 is formed between the two parts. Two diametrically opposed slots 7 are formed on the same portion 1c close to the step 6, while two further diametrically opposed slots 8 are formed near the open end of the outer housing 1.

The side wall of the end portion 1b of the outer housing 1 is formed with two diametrically opposed side grooves 9 and two tabs 10 projecting from the side surface of a tubular member 11 engage therewith. Tubular member 11 is open at its distal end and closed by a wall 11a at its proximal end. With reference also to FIGS. 5, 8a and 8b, the tubular member 11 is coaxially engaged within the tubular outer housing 1 and wall 11a is formed with two holes 12 for a fixed connection with the ends of the two knob pins 4 passing through the arc grooves 2, whereby the tubular member 11 is integral to knob 3 and can angularly displace with it but cannot axially slide due to the bent-out tabs 10 engaging with the side grooves 9 of the outer housing 1.

Two diametrically opposed, circumferential slots 13 are formed on the lateral surface of the tubular member 11 at an intermediate position and respective through guides 14 extend diagonally along the side surface of the tubular member 11 toward the distal end thereof, each with an angular extension of about 90°. The two through guides 14 have equal slope, but are symmetrically opposed relative to longitudinal axis X.

The two through guides 14 are formed each by a first and a second inclined tract 14a and 14b separated by an intermediate step 14c lying on a plane orthogonal to the longitudinal axis X and an end tract 14d extending longitudinally from the end of the second tract 14b to the open end of the tubular member 11.

The first inclined tract 14a of the through guides 14 starts from an intermediate position of the respective circumferential slots 13 and defines in this way two slot parts 13a and 13b placed at the right side and at the left side of the first tract 14a. A flap 15, the function of which will be explained later on, extends out from the lower side of the slot part 13b close to the first tract 14a.

Figures 10A, 10B, 10C:
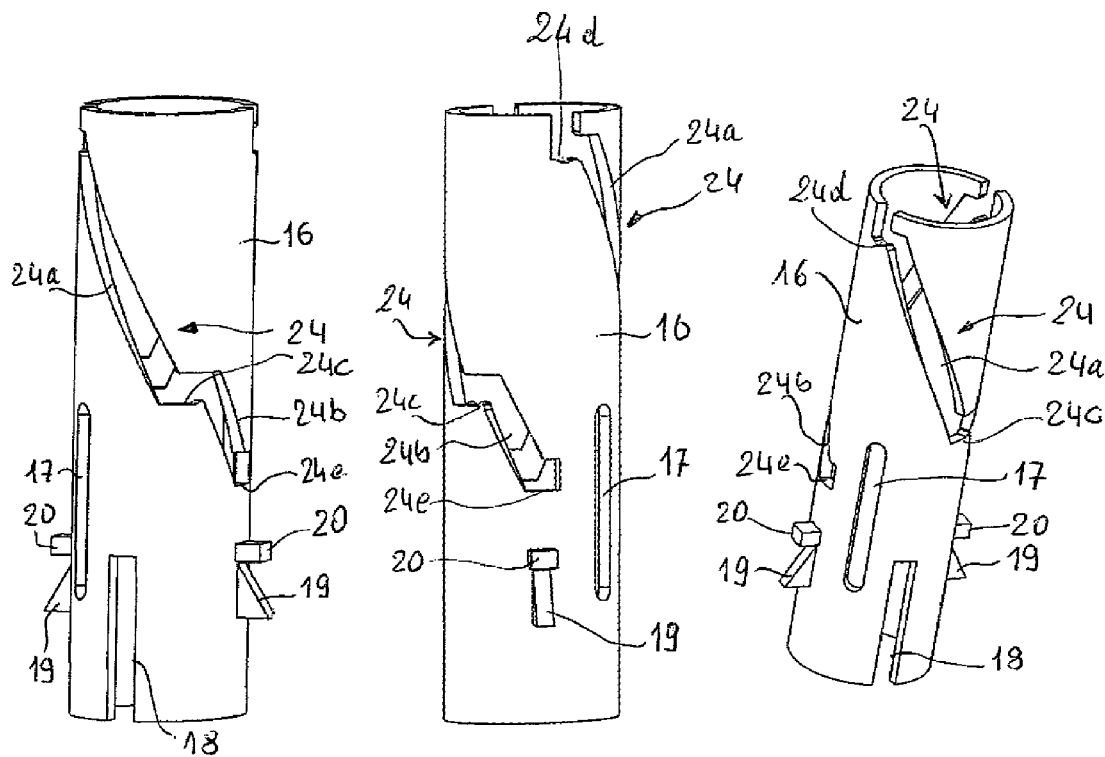
FIGS. 10a, 10b and 10c show, in two longitudinal views axially rotated by 90° and a perspective view, the inner housing of the autoinjector device according to the invention.

An inner housing 16 of tubular shape with open ends, shown in detail in FIGS. 10a, 10b and 10c, is coaxially housed in the tubular member 11. Two diametrically opposed, longitudinal grooves 17 are formed on the inner housing 16 and at least a longitudinal cut 18, serving as viewing window for the drug extends from the distal end thereof. Two radial teeth 19 extend outwardly from the inner housing 16 for engaging within the slots 7 of the outer housing 1, preventing the inner housing 16 from moving linearly and rotationally relative to the outer housing 1. A pair of radial projections 20 extend from inner housing 16 to rest against the step 6 (see FIG. 4) of the outer housing 1 to further prevent any axial movement.

Figure 6:
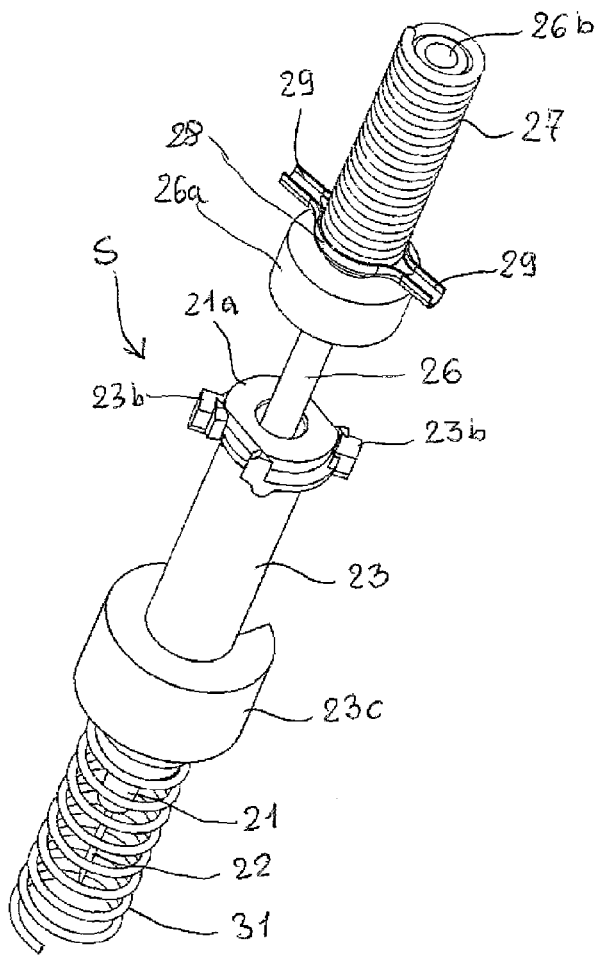
FIG. 6 is a perspective view of the syringe assembly mounted in the autoinjector device according to the invention.

With reference to FIG. 6, a syringe assembly S is shown therein. The assembly comprises a syringe 21 with a needle 22 at its distal end. The syringe is housed in a tubular support 23, also shown in FIG. 9, open at its ends and having an intermediate enlargement 23c fitting against the distal end of the inner housing 16, wherein the tubular support 23 is partly housed. A window 23d is formed on tubular support 23 and is aligned to longitudinal cut 18 of inner housing 16 to make the syringe content visible from the outside.

The tubular support 23 is formed with bent-in edges 23a at its distal end against which the syringe distal end abuts, while two opposed radial projections 23b are formed at the other end on which a flange 21a of the syringe 21 rests.

The two radial projections 23b of the tubular support 23 are further configured to be slidably engaged within the longitudinal grooves 17 of the inner housing 16 to allow the tubular support 23 to axially move for a set extent, whereby the syringe housed therewith is correspondingly moved.

Two inclined guides 24 are formed on the wall of the inner housing 16 at diametrically opposed parts, said guides being inclined relative to the longitudinal axis X, but not incident thereto, because they are formed on the lateral surface of the inner housing 16. In particular, as shown in FIGS. 10a and 10b, each inclined guide 24 comprises a first and a second ramp 24a and 24b separated by an intermediate land 24c and ending with two end lands 24d and 24e formed at the beginning of the first ramp 24a and, respectively, at the end of the second ramp 24b. The first ramp 24a has a length greater than the second ramp 24b. The inclined guides 24 have equal inclination and a substantially equal extension of the through guides 14 of the tubular member 11.

Inside the syringe 21 a plunger stopper 25 is slidably and sealingly housed and is connected to the end of a plunger 26 axially sliding within the inner housing 16. In particular the plunger 26 has an enlarged intermediate portion 26a of a substantially cylindrical shape and diameter substantially equal to the inner diameter of the inner housing 16 in order to keep the plunger in axial alignment to the inner housing 16 when sliding therein.

As shown in FIG. 6, at the end opposed to that bearing the stopper 25 the plunger 26 has an axial stem 26b with an injection spring 27 arranged around it and placed between the wall 11a of the tubular member 11 and a cam plate 28 coaxially and slidably mounted on the stem 26b and placed close to the enlargement 26a of the plunger 26. The injection spring 27 is mounted in a compressed state between the wall 11a and the cam plate 28 and therefore is pre-loaded when the device is in the rest or storage condition.

Two slide pins 29 extend radially from cam plate 28 at diametrically opposed sides thereof and are configured to rest on flaps 15 of the tubular member 11 when the device is in the rest or storage condition and to be able to slide in the respective inclined guide 24 of the inner housing 16.

The inner housing 16, which houses the syringe support 23 and the syringe 21 therein, both slidable in the axial direction, is arranged in the trigger slide 30 that is shaped with the tapered end from which the syringe needle 22 extends when the device is used. The syringe support 23 projects from the inner housing 16 starting from its intermediate enlargement 23c, which has an essentially cylindrical shape and a diameter substantially equal to the inner diameter of the trigger slide 30 to allow for the relative sliding while keeping the axial alignment.

A push-back spring 31 is placed between the intermediate enlargement 23c of the syringe support 23 and the tapered end of the trigger slide 30 in order to keep the syringe support 23 biased against the end of the inner housing 16. From the trigger slide 30, near its tapered end, there extend two diametrical teeth 32 (only one visible in FIG. 1) which engage slidably in the slots 8 of the outer housing 1, whereby the trigger slide 30 is enabled to slide axially over a distance equal to the length of the slots 8 relative to the outer housing 1.

Figure 7:
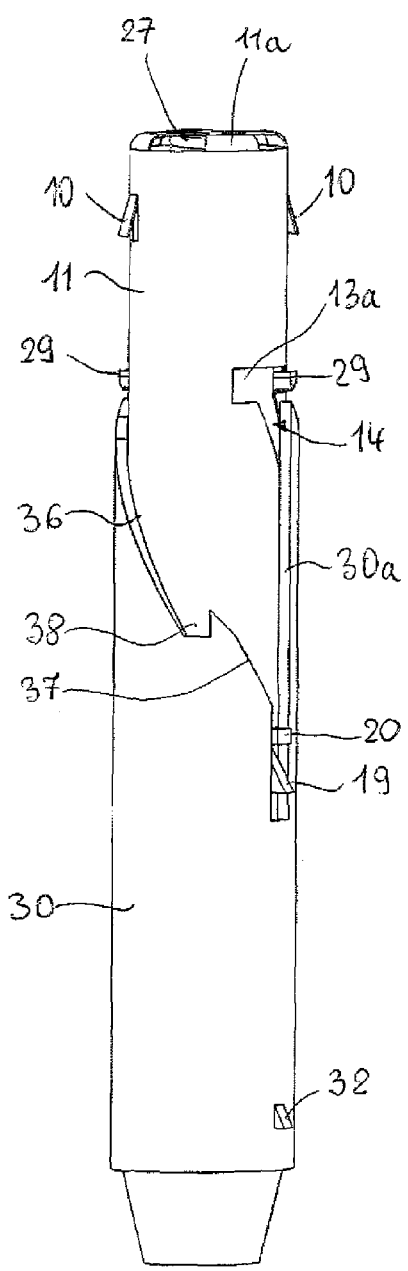
FIG. 7 is a partial side view of the autoinjector device according to the invention with parts removed for clarity.

The other end (the proximal end) of the trigger slide 30, which has a substantially tubular shape, is arranged between the outer housing 1 and the tubular member 11 and is configured in the shape of legs, which, in the present embodiment of the invention, are formed with sloped profile having substantially the same inclination as that of the inclined guides 24 formed on the inner housing 16. In particular, as shown in FIG. 7, starting from said end the trigger slide 30 is formed with two diametrically opposed, longitudinal cuts 30a defining two portions of tubular surface each delimited by a first side coinciding with a generatrix of the tubular trigger slide and a second side inclined relative to said generatrix. The inclined side of each tubular surface portion is formed by a long leg 36, starting from the proximal end of the trigger slide 30, and a short leg 37 separated by a recess 38.

When the autoinjector is operated, the slide pins 29 of cam plate 28 coaxial to stem 26b of plunger 26 slidingly engage, as said before, in the respective inclined guides 24 of the inner housing 16 passing through the through guides 14 of the tubular member 11 and abutting against the inclined profiles of the respective long and short legs 36 and 37 of the trigger slide 30.

In summary, knob 3 and tubular member 11 are integral to each other and pivotable relative to the outer housing 1 and the tubular member 11 is unable to axially slide relative thereto. The inner housing 16 is fixed relative to the outer housing 1 and therefore is unable to move linearly and rotationally relative thereto. The trigger slide 30 is axially slidable relative to the outer housing 1, but cannot rotate relative thereto, and the syringe support 23 is slidable axially in the inner housing 16 and in the trigger slide 30 against the push-back spring 31. The plunger 26 is axially slidable in the inner housing 16 under the action of the injection spring 27 once it is triggered. Since the inner housing 16 is fixed to the outer housing 1, the sliding of the slide pins 29 on the inclined profiles of the legs 36 and 37 and within the inclined guides 24 of the inner housing 16 causes the syringe support 23 and the plunger 26 to axially move.

The operation of the autoinjector device according to the invention is now described with reference to FIGS. 11 to 22.

Figure 11:
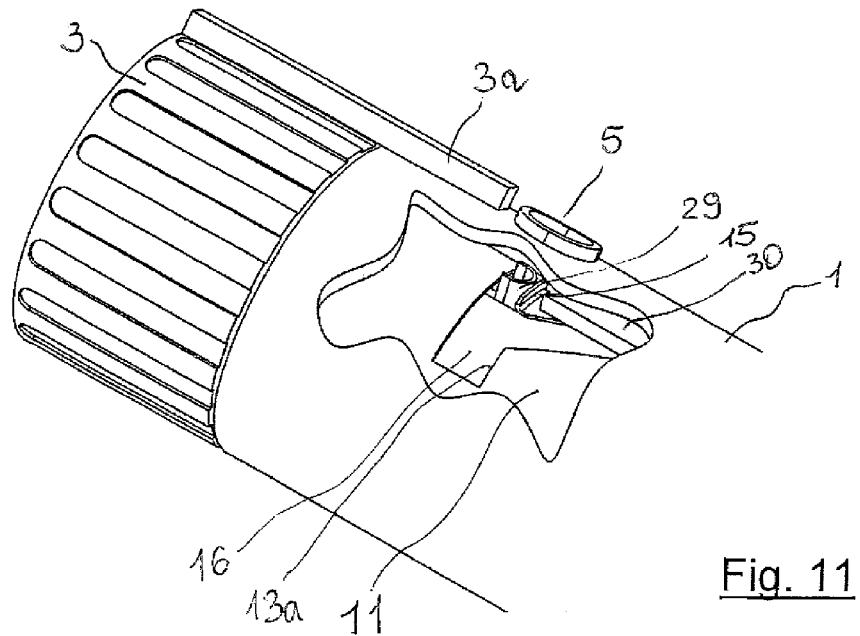
FIGS. 11 to 22 show the operational steps of the autoinjector device according to the invention.
Figure 12:
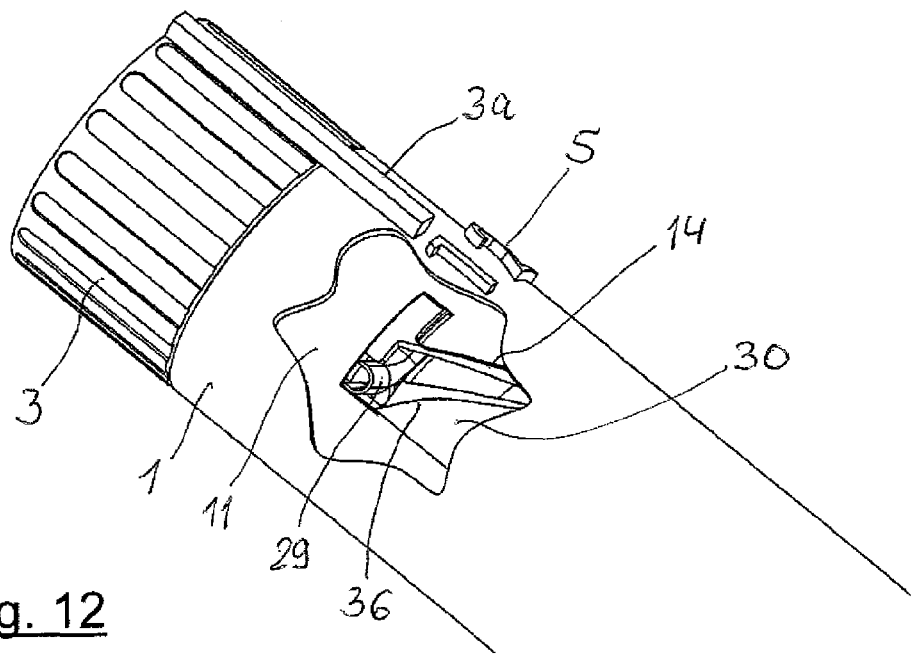

In the stored condition, the injection spring 27 rests in a fully compressed state between the wall 11a of the tubular member 11 and the cam plate 28, as shown in FIG. 3. The slide pins 29 of the cam plate 28 rest on the bent-out flaps 15 of the tubular member 11, thereby securing the injection spring 27 in place (FIG. 11). This to prevent creep of the mechanism over a medium to long-term storage period. The stem 26a of the plunger 26 also helps to prevent the compressed injection spring 27 from deflecting. The tubular member 11 is connected to the outer housing 1 through the projecting tabs 10 clipped in the grooves 9 to allow the rotation and prevent the translation of the tubular member 11 with respect to the outer housing 1, when the knob 3 is rotated.

The inner housing 16 sits in the tubular member 11 and is fixed to the outer housing 1 by the teeth 19 and projections 20 preventing them from rotating and translating relative to each other.

The support 23 of the syringe 21 is seated in the trigger slide 30 and slidingly engages its radial projections 23b in the longitudinal grooves 17 of the inner housing 16. The length of these grooves defines how far the syringe support 23 can move which ultimately sets the needle extension distance.

Once the protective sheath 40 is removed, to perform the first automatic injection the user must remove the needle cap 41 from the tapered end of the trigger slide 30. In this step the needle is uncovered, but remains sub-flush within the tapered end of the trigger slide.

To arm the device for the first dose, the user must rotate the cap-shaped knob 3 by a set angle. Twisting the knob 3 from the position 0 (stored state) to position 1 (first dose armed state) causes the tubular member 11 to rotate a corresponding set angle, as it is integrally linked to the knob 3 (FIG. 12), and the alignment of the first inclined tract 14a of the through guides 14 to the first ramp 24a of the inclined guides 24. This action causes the slide pins 29 of the cam plate 28 to drop from the bent-out flaps 15 of the tubular member 11 onto the respective first lands 24d of the inclined guides 24 of the inner housing 16, thereby allowing the injection spring 27 to decompress a small set distance. In this step no other components change position or orientation. The device is now armed and ready to be triggered by the user.

Figure 13:
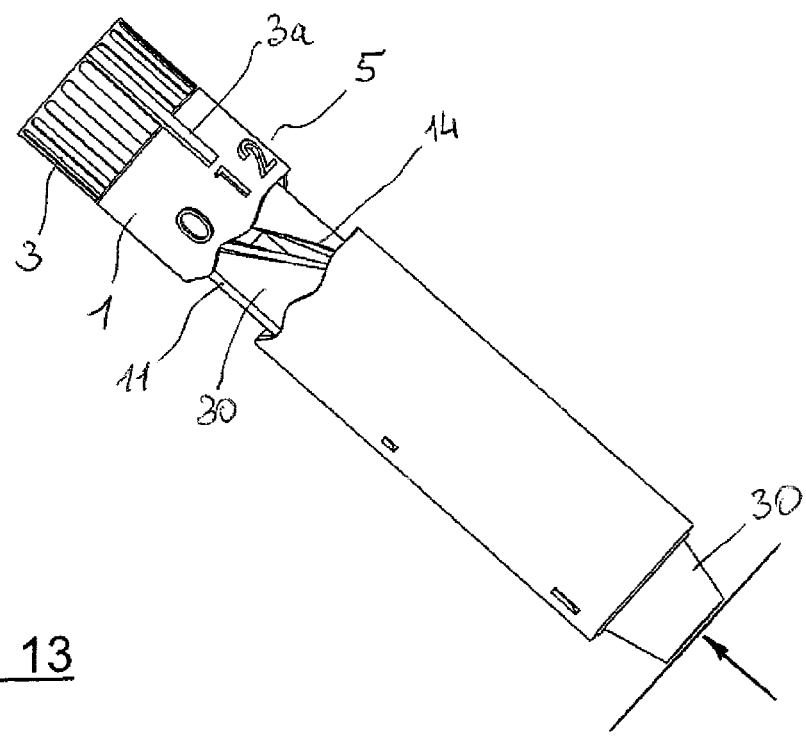
Figure 14:
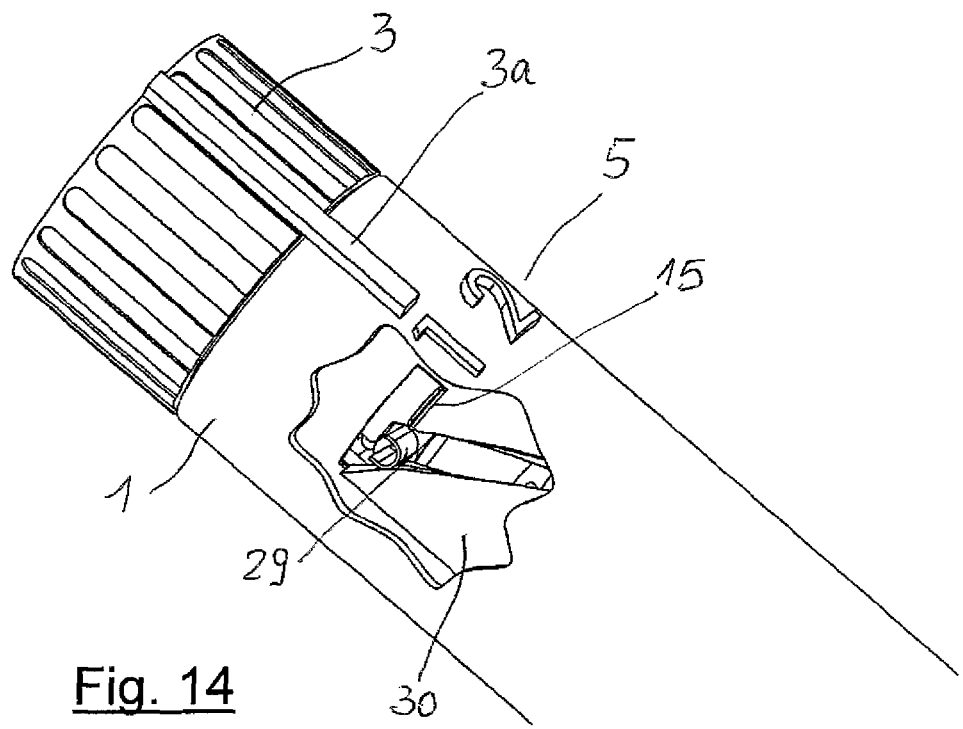

The device is triggered by the user pressing the tapered end of the trigger slide 30 against the injection site (FIG. 13). Depressing the trigger slide 30 forces the component to move inside the outer housing 1 towards the opposite end. This causes the ends of the long legs 36 of the trigger slide 30 to exert a side force against the slide pins 29 of the cam plate 28, which rotates around stem 26b to arrange the pins 29 into alignment to the first ramp 24a of the inclined guides 24 of the inner housing 16 (FIG. 14), whereby these pins 29 are free to slide in the first ramp 24a under the action of the injection spring 27.

Figure 15:
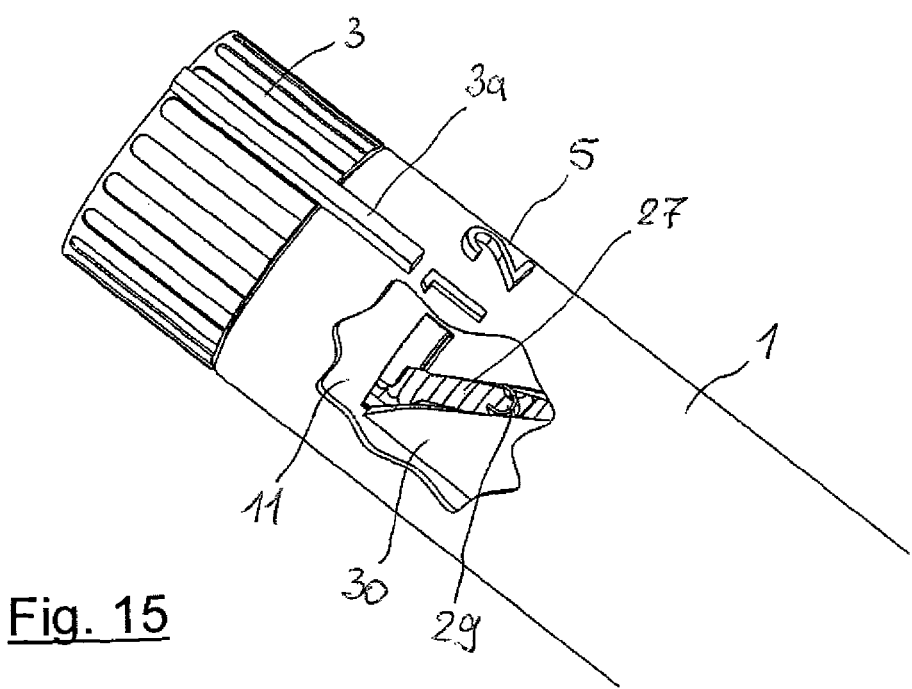
Figure 16:
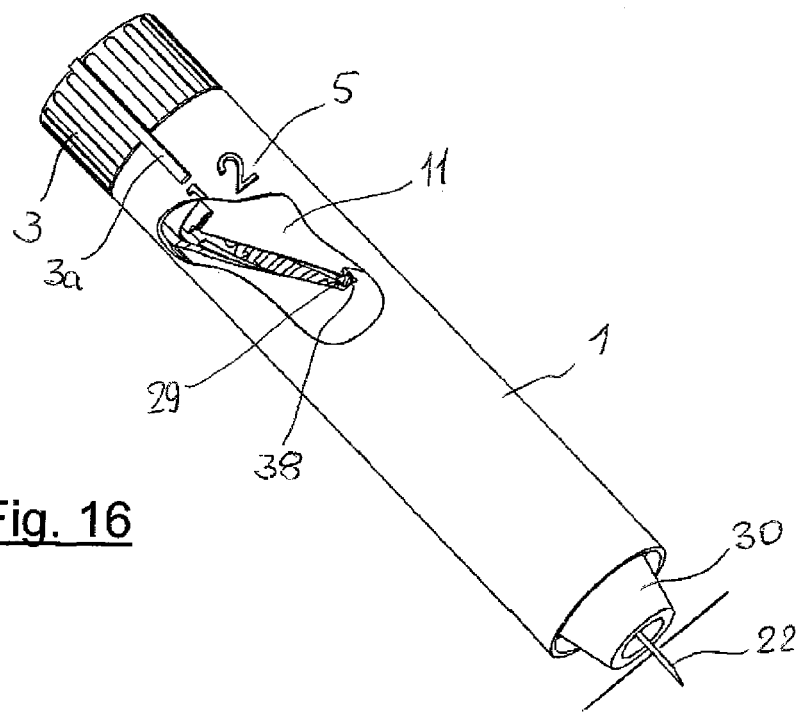

Once triggered, the injection spring 27 is free to decompress and thereby forces the cam plate 28, the plunger 26 and the syringe 21 forward, i.e. toward the distal end of the outer housing 1 (FIG. 15). This movement also causes the syringe needle 22 to enter the injection site by a depth governed by the length of the longitudinal grooves 17 guiding the syringe support 23 on the inner housing 16. In order that this movement can occur, the hydrostatic force required to expel the medicament from the syringe needle must be greater than the sum of the frictional forces to push the syringe assembly S forward to the specified needle injection depth.

Once the syringe needle 22 reaches the full injection depth (FIG. 16), the injection spring 27 continues to decompress pushing the cam plate 28 and the plunger 26 forward with respect to the syringe barrel and causing the first dose of medicament to be expelled from the syringe. It is worth noting that the cam plate 28, while axially moving, rotates around the stem 26a of the plunger 26, as the slide pins 29 are constrained to slide in the inclined guides 24. It is also worth noting that the length of the ramp 24a of the inclined guides 24 is such as to allow both the sliding of the syringe support 23, to cause the needle to penetrate the skin, and the sliding of the plunger 26 to delivery the first drug dose.

Figure 17:
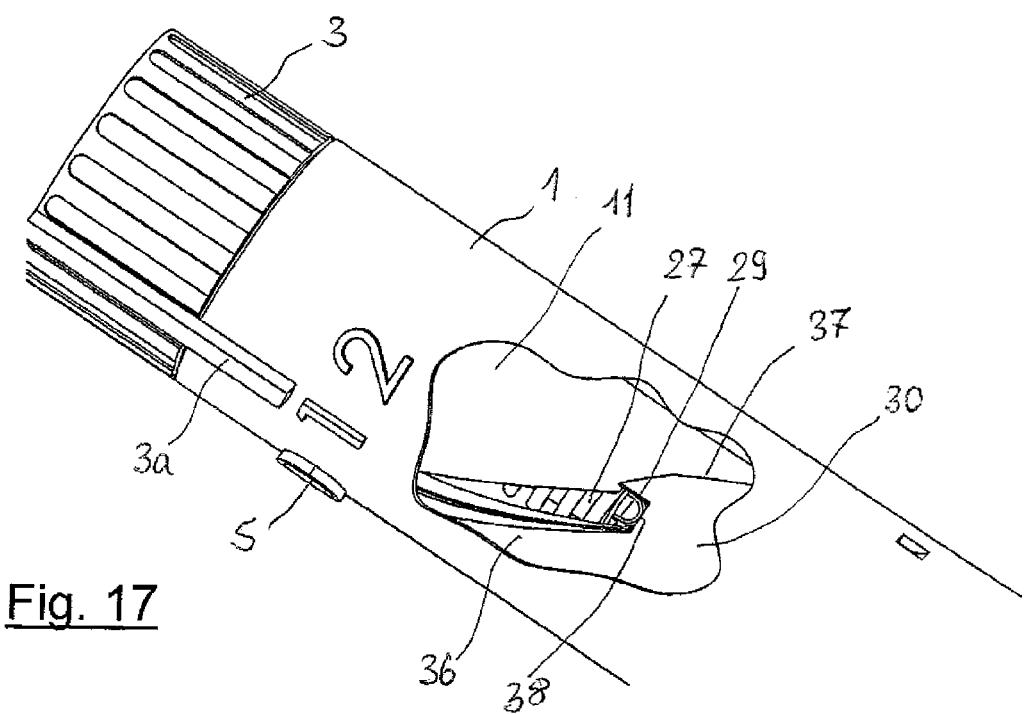

The first dose delivery is complete once the slide pins 29 reach the intermediate land 24c of the inclined guides 24 on the inner housing 16 and the recess 38 of the trigger slide 30 (FIG. 17). As the land 24c prevents the injection spring 27 from decompressing any further and the engagement in the recess 38 prevents the slide pins 29 from rotating any further, no more medicament will be expelled.

Figure 18:
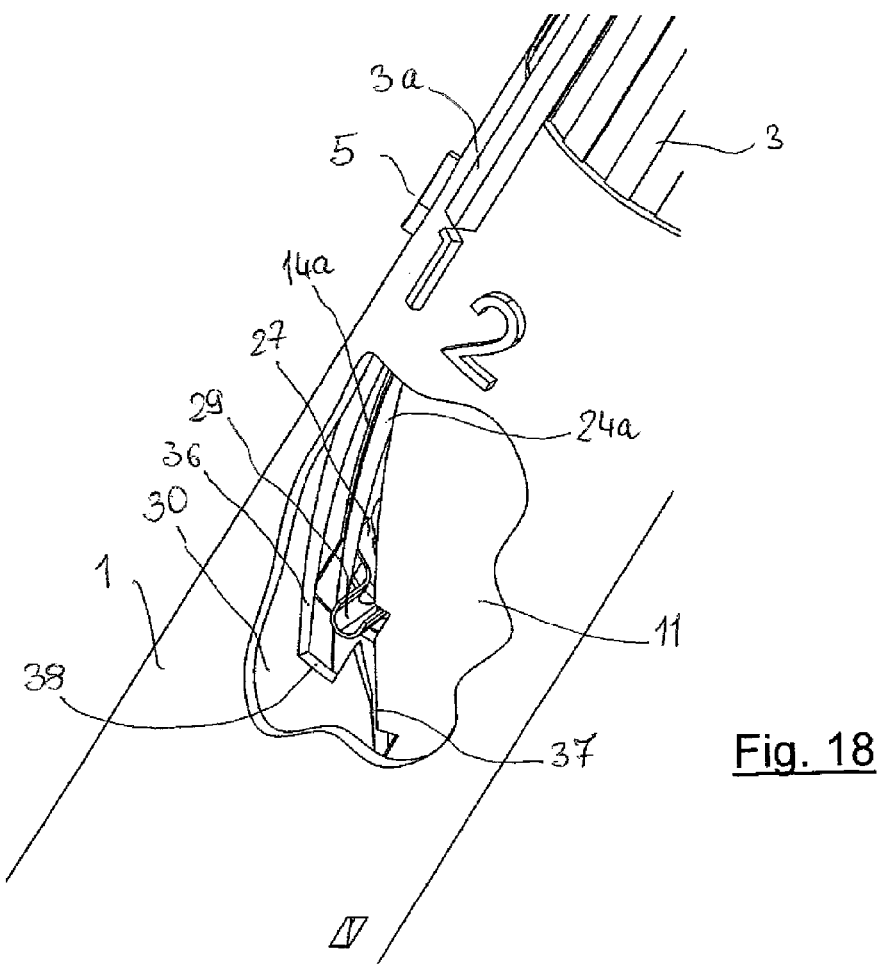

After delivery of the first dose, the user removes the device from the injection site. Since the pressure on the tapered end of the trigger slide 30 ceases, the push-back spring 31 moves forward the tapered end reducing the exposed needle length. Due to this sliding of the trigger slide 30, the slide pins 29 come out from the respective recesses 38, while being stopped on lands 24c of the guide 24, as shown in FIG. 18. Then the user re-sheaths the device in the protective sheath 40 to avoid any needle damaging or injuries and waits for a prescribed time to decide if a second dose is necessary.

Figure 19:
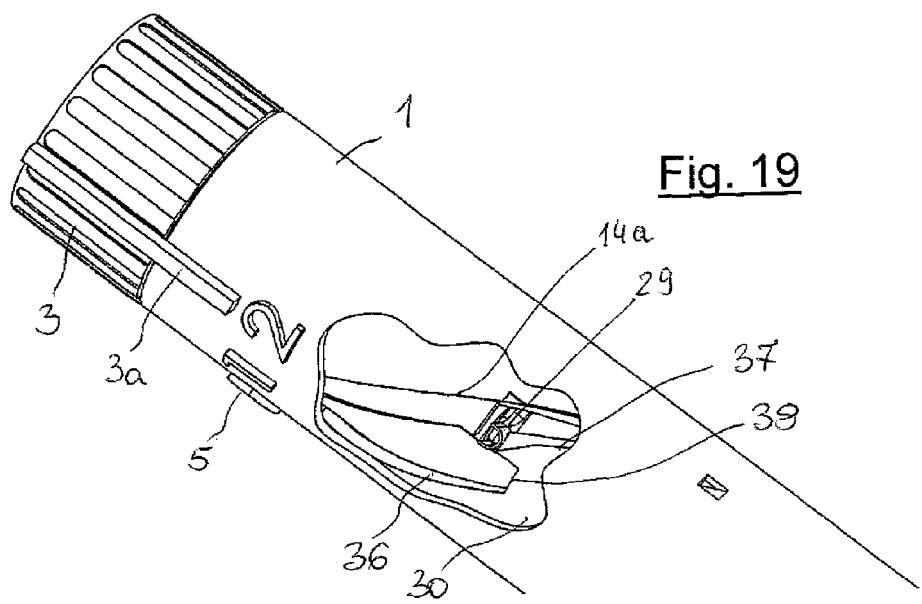
Figure 20:
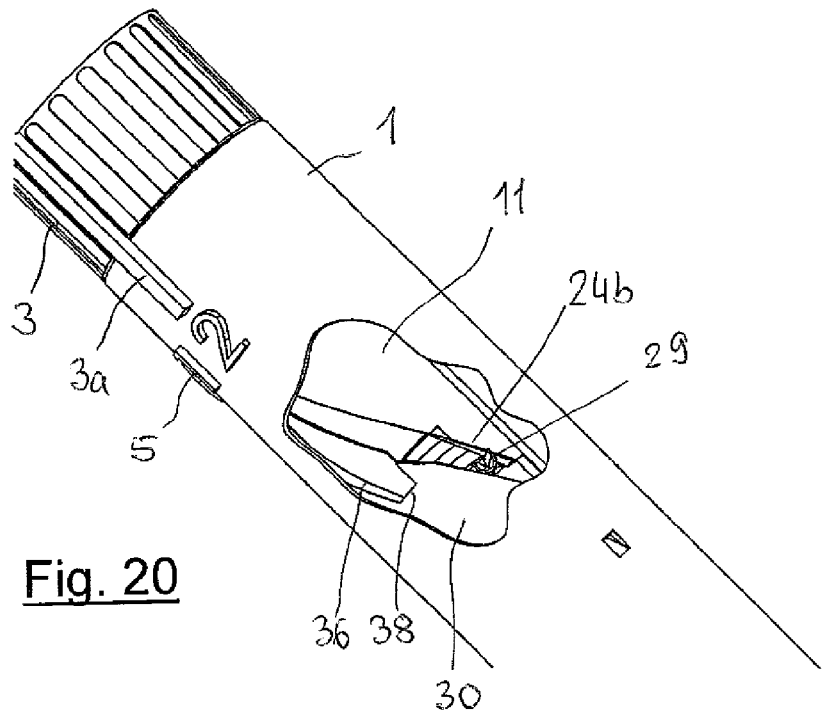

Should a second dose be required, the user must first remove the protective sheath 40 from the device in order to access the needle and then arm the device to prepare it for the second dose delivery. To this purpose the user must rotate the cap-shaped knob 3 by a prefixed angle. Rotating the knob 3 from position 1 to position 2 (second dose injecting armed state) causes the tubular member 11 to rotate a set angle. In this way the second inclined tract 14b of the through guides 14 is aligned to the ramp 24b of the inclined guides 24 and the slide pins 29 move along the intermediate land 24c up to reach a position ready to be triggered (FIG. 19).

The device is triggered by the user pressing the tapered end of the trigger slide 30 against the injection site and causing the trigger slide to move toward the opposite end of the outer housing 1. The end of short legs 37 of the trigger slide 30 comes into contact with the respective slide pin 29 and displaces it laterally on the intermediate land 24c up to bring it into alignment to the second ramp 24b of the inclined guide 24 on the inner housing 16, thus allowing the slide pins 29 to freely move in the respective second ramps 24b (FIG. 20) under the action of the injection spring 27 which depresses further. In this way a further sliding of the cam plate 28 and the piston 26 relative to the syringe barrel is caused to expel the medicament from the syringe, i.e. the delivery of the second dose. It is worth noting that, since the needle remains exposed from the first dose, there is no need to push the syringe assembly forward and therefore a lower length of the second ramp 24b with respect to the first ramp 24a is necessary.

Figure 21:
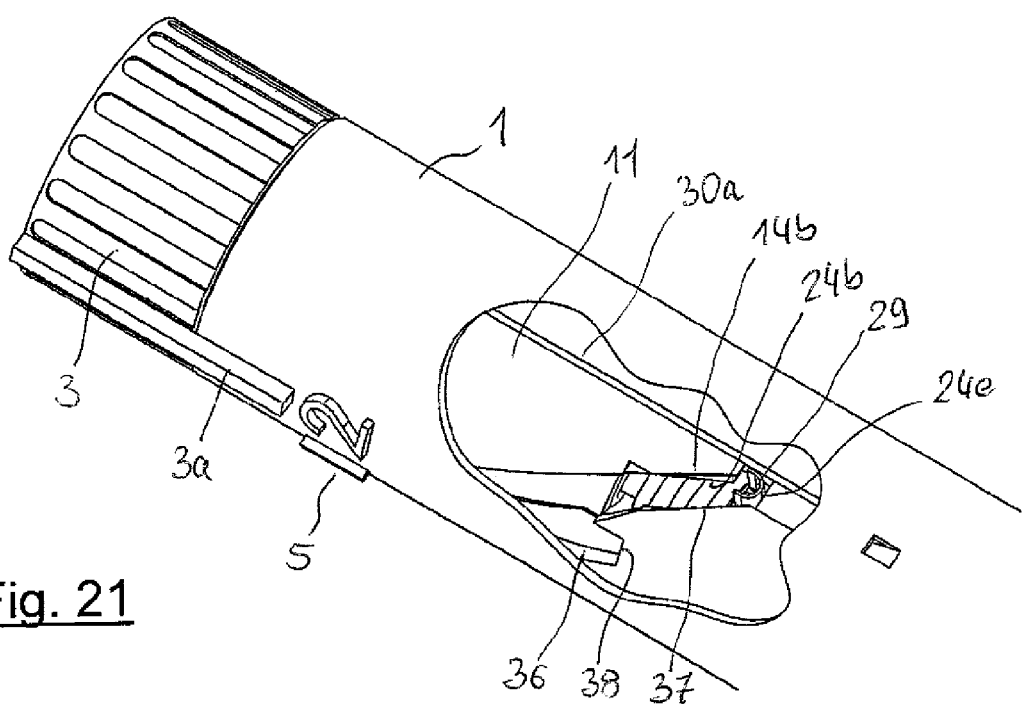

The delivery of the second dose is complete once the slide pins 29 reach the end land 24e of the inclined guides 24 on the inner housing 16 (FIG. 21). As the end land 24e prevents the injection spring 27 from decompressing any further, no more medicament will be expelled.

Figure 22:
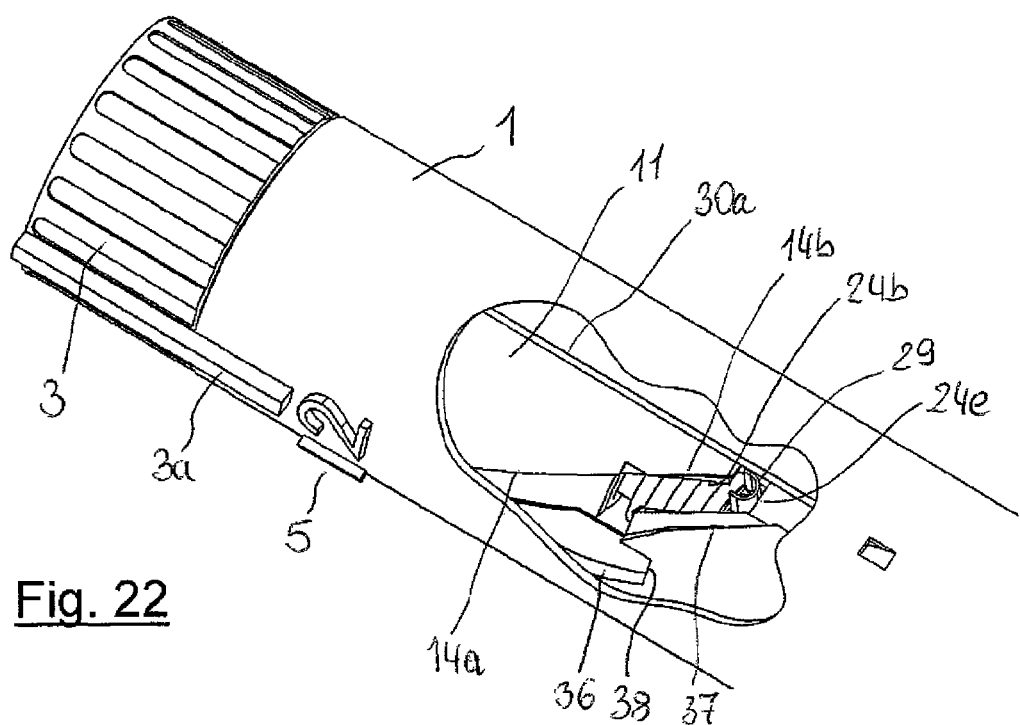

After delivery of the second dose, the user removes the device from the injection site. As the pressure on the tapered end of the trigger slide 30 ceases, the push-back spring 31 moves forward the tapered end (FIG. 22). Finally, the user re-sheaths the device for its safe disposal.

The tubular member 11 is preferably made of metallic material to provide adequate protection to the syringe and to ensure a long-term storage of the device, as it is not prone to creep to the same extent that the other moulded device components would be.

The autoinjector device according to the invention is suitable to the delivery of medicaments in solution, especially epinephrine (also known as adrenaline).

In particular, the doses of epinephrine that can be administered with the device of the invention are preferably in the range of 0.05 mg to 0.5 mg for each delivered dose (from 0.1 mg to 1 mg if two doses are considered).

Preferred doses for each delivery are 0.05 mg, 0.10 mg, 0.15 mg, 0.30 mg and 0.50 mg.

The above doses are based on a concentration of the epinephrine solution preferably ranging from 0.05 mg/ml to 0.5 mg/ml, the concentrations 0.05 mg/ml, 0.1 mg/ml, 0.16 mg/ml, 0.3 mg/ml and 0.5 mg/ml being particularly preferred.

The invention claimed is:

1. A medicament injector device comprising
    a syringe assembly comprising a needle and adapted to contain a medicament to be injected, said assembly being coaxially and slidably arranged in an outer housing extending along a longitudinal axis,
    arming means for arming the medicament injector device from a rest position to a first dose injecting armed position and to a second dose injecting armed position, said arming means being placed at one end of said outer housing,
    first elastic means between said syringe assembly and said arming means, said first elastic means being in a compressed state when the medicament injector device is in the rest position,
    device drive means for controlling the sliding of said syringe assembly from said armed positions to inject the the needle in an injection site and deliver the first dose and, if necessary, deliver the second dose at a subsequent set time,
    wherein the syringe assembly comprises slide means engaged in stepped guide means, said guide means being inclined, but not incident, relative to a direction of the longitudinal axis and axially integral with said outer housing, said slide means and said guide means being pivotable relative to each other about the longitudinal axis, said device drive means being capable to slide axially as a result of separate and successive pressures against said injection site to cause a first relative displacement of said slide means from said first dose injecting armed position to a position of alignment to said guide means,
    wherein said slide means are freely moveable along the guide means up to a first stop position, and a second relative displacement of said slide means from said second dose injecting armed position to a position of alignment to said guide means, and
    wherein said slide means are freely moveable along the guide means up to a second stop position.

2. The injector device according to claim 1, wherein said slide means are axially pivotally mounted on said syringe assembly and said guide means are rotationally integral with said outer housing.

3. The injector device according to claim 1, wherein said guide means comprise an inner housing, on which a guide track is formed, said guide track comprising an intermediate land separating a first and a second ramp of said guide track and two end lands on which said slide means abut in said first dose injecting armed position and after the delivery of the second dose.

4. The injector device according to claim 3, wherein the first ramp of said guide track has a length greater than the second ramp of said guide track.

5. The injector device according to claim 1, wherein said drive means comprise axial legs configured to act on said slide means to displace said slide means from said first dose injecting armed position and, subsequently, from said second dose injecting armed position as a result of respective axial movements of said drive means.

6. The injector device according to claim 1, wherein said syringe assembly comprises a syringe seating in a syringe support axially sliding relative to said outer housing, said syringe comprising said needle and a plunger slidably and sealingly engaged therein and extending from the syringe with an axial stem on which said slide means are mounted.

7. The injector device according to claim 6, wherein said slide means are pivotally mounted on said stem said plunger.

8. The injector device according to claim 1, wherein said slide means comprise a cam plate with two slide pins radially projecting at diametrically opposed sides for engaging with said guide means, said first elastic means comprising a compression spring coaxial to said stem between said plate and said device arming means.

9. The injector device according to claim 1, wherein said drive means comprise a trigger slide slidable between said outer housing and said inner housing and projecting from the other end of the outer housing, the injector device further comprising second elastic means between said syringe assembly and said trigger slide to keep the trigger in a projected condition from said outer housing.

10. The injector device according to claim 9, wherein said trigger slide comprises a first couple of diametrically opposed axial legs and a second couple of diametrically opposed axial legs, for causing the first and, respectively, the second displacement of said slide means.

11. The injector device according to claim 10, wherein the axial legs of said first couple of legs are longer than the axial legs of said second couple of legs and are configured with an inclined profile in a way substantially equal to that of said first ramp and, respectively, of said second ramp of said guide track.

12. The injector device according to claim 11, wherein
an inclined profile of a long leg and an inclined profile of a short leg extend one after the other and
a recess is formed therebetween for engaging a respective slide pin at the end of its run along the first ramp of said guide track.

13. The injector device according to claim 1, wherein said device arming means comprise
a knob pivotally mounted on said outer housing,
a tubular member integral to said knob and extending between said outer housing and said inner housing coaxially thereto,
a pair of diametrically opposed through guides formed on said tubular member having inclinations substantially equal to that of said guide tracks and extending from circumferential slots lying on a plane orthogonal to the longitudinal axis, said through guides each comprising two inclined tracts having the same length as that of said first and second ramp of said guide tracks, a step being formed therebetween corresponding to the intermediate land of said guide tracks.

14. The injector device according to claim 13, wherein said circumferential slots are formed with respective projecting flaps on which the slide pins rest when the device is in the rest position.

15. The injector device according to claim 13, further comprising
angularly spaced reference marks on said outer housing corresponding to said rest position and said first dose injecting and second dose injecting armed positions and
a pointer extending from said knob, said pointer being alignable to each of said reference marks as a result of a preset angular displacement of said knob.

16. The injector device according to claim 13, wherein said tubular member is made of metal.

17. The injector device according to claim 1, further comprising a removable cap at the end of said trigger slide extending from said outer housing for protection of the needle.

18. The injector device according to claim 1, further comprising a removable protective sheath on said outer housing at the end where said trigger slide projects from.

* * * * *